United States Patent [19]

Kubo

[11] Patent Number: 5,300,052
[45] Date of Patent: Apr. 5, 1994

[54] URINARY COLLECTOR FOR MEN
[75] Inventor: Yoshinori Kubo, Oumeo, Japan
[73] Assignee: Alcare Co., Ltd., Tokyo, Japan
[21] Appl. No.: 969,021
[22] Filed: Oct. 30, 1992
[30] Foreign Application Priority Data Nov. 1, 1991 [JP] Japan .................. 3-313471

[51] Int. Cl.⁵ .......................... A61F 5/44; A47K 11/00
[52] U.S. Cl. .................. 604/349; 604/347; 604/350; 604/351; 4/144.1; 4/144.3
[58] Field of Search ............... 604/322-323, 604/332-333, 335, 347, 349-351; 4/144.1, 144.2, 144.3, 144.4

[56] References Cited

U.S. PATENT DOCUMENTS

| | | | |
|---|---|---|---|
| 1,490,793 | 4/1924 | Ajamian et al. | 604/350 |
| 2,873,740 | 2/1959 | Wainwright | 604/347 |
| 3,340,876 | 9/1967 | Hill | 604/347 |
| 3,613,123 | 10/1971 | Langstrom | 4/144.3 |
| 4,257,418 | 3/1981 | Hessner . | |
| 4,378,018 | 3/1983 | Alexander et al. . | |
| 4,419,100 | 12/1983 | Alexander . | |
| 4,475,910 | 10/1984 | Conway et al. . | |
| 4,490,148 | 12/1984 | Beckestrom . | |
| 4,627,846 | 12/1986 | Ternstrom . | |
| 4,932,948 | 6/1990 | Kernes et al. . | |

FOREIGN PATENT DOCUMENTS

| | | |
|---|---|---|
| WO8103273 | 11/1981 | PCT Int'l Appl. . |
| WO8503428 | 8/1985 | PCT Int'l Appl. . |
| WO8606620 | 11/1986 | PCT Int'l Appl. . |
| 1571657 | 7/1978 | United Kingdom . |
| 8430821 | 12/1984 | United Kingdom . |

Primary Examiner—Randall L. Green
Assistant Examiner—P. Zuttarelli
Attorney, Agent, or Firm—Haverstock, Garrett & Roberts

[57] ABSTRACT

A urinary collector device for men including a urinary collector body formed into a bag shape and constructed of soft, flexible water-proof material, the urinary collector body having a first or upper portion formed into a penis receiving chamber which includes an opening for enabling a penis to be inserted therethrough into such chamber. The urinary collector body also includes a second opposite or lower portion which forms a urinary flow chamber which is separated from the penis receiving chamber by a water permeable membrane. The urinary flow chamber is packed with hydrophobic material having a plurality of passages therethrough and includes a urinary discharge outlet. The penis receiving opening further includes an annular sleeve therearound for cooperatively engaging and forming a sealed condition around a penis when inserted therein, the packed hydrophobic material in the urinary flow chamber maintaining the shape of the device even as a penis is inserted therein and when the device is worn under clothing. Urine discharge flows into the penis receiving chamber and thereafter passes through the water permeable membrane into the urinary flow chamber. Once in the urinary flow chamber, the flow of urine is buffered by passage through the hydrophobic material and is thereafter discharged from the urinary flow chamber through the urinary discharge outlet.

12 Claims, 4 Drawing Sheets

URINARY COLLECTOR FOR MEN

Applicant hereby claims foreign priority benefits under 35 USC §119 of corresponding Japanese patent application Serial No. (Hei) 3-313471, filed Nov. 1, 1991.

BACKGROUND OF THE INVENTION

1. Field Of The Invention

The present invention relates to a urinary collector for men and, more particularly, to various embodiments of a collector device which can be worn discretely under clothing and undergarments to receive urinary discharges, and comfortably, yet securely, attaches and forms a sealed condition around the penis such that the rest of the genitalia and pelvic region are not exposed to urine. The device buffers the flow of the urine from the penis without the urine backflowing and accumulating around the penis such that the penis can remain relatively dry and sanitary, and the device smoothly and evenly discharges the urine directly to other urine receiving and holding means such as a urinal bag or the like. The collector is particularly adaptable for use on men who, for instance, have a urinary incontinence condition such as due to injury, disease and the like, who are bedridden or are not sufficiently mobile or ambulatory to walk to a restroom or latrine such as due to age, or physical handicaps, and who suffer from dysuria which is difficulty or pain in discharging urine.

2. Description Of The Prior Art

Known urinary collector devices for men include appliances having a urine receiving portion or member which wraps around or otherwise secures to the penis for receiving urine therefrom, a bag attached to the receiver for collecting the discharged urine, and means such as a belt for securing the appliance to a body portion such as the hypogastrium, as disclosed in Japanese Unexamined Patent Application Publication Nos. Sho 57-209051; Sho 58-130037; Sho 61-137558; Hei 1-284267; and Sho 57-500911. Limitations of such prior art urinary collector appliances include, however, large and cumbersome size and relatively complex belts and other attachment means which make for difficult attachment and removal of the appliance. Other limitations of such prior art devices include discomfort due to the use of rubber as a construction material which provides the required water resistant characteristics and which enables adhesion of the appliance to the body of the wearer.

Other prior art urinary collectors for men include diaper and diaper-type apparel of cloth, paper, and other absorbent materials, which are formed and shaped to be worn about the pelvic region, such as disclosed in Japanese Unexamined Patent Application Publication Nos. Sho 59-25741; Sho 4-10596; Sho 60-18166; Sho 61-501130; and Sho 62-602855. Such prior art diapers are simple in construction, comfortable and pleasing to the touch. However, an important limitation of such diapers is that urine discharged into the diaper spreads over much of the diaper surface so as to greatly decrease and impair the comfort and feel thereof. Another shortcoming of diapers is the relatively labor intensive requirements for placement and removal thereof from the body, which requirements can be particularly extenuating for dysuriac persons, and bed-ridden or feeble persons. Furthermore, another limitation is that persons afflicted with dysuria may be conscientious of the appearance of such diapers under clothing.

SUMMARY OF THE INVENTION

The present urinary collector device for men overcomes many of the above discussed disadvantages and shortcomings associated with the known prior art devices and teaches the construction and operation of an improved urinary collector device for men which can be comfortably and discretely worn and which effectively receives and buffers the discharged urine flow without backflow and drains the urine into a urinal bag or other collecting means.

The present urinary collector for men provides a urinary collector body portion which is made of waterproof, soft material and which is formed into a bag or bag-like shape. The urinary collector body includes a penis receiving chamber located in a first or upper part of the collector body, which penis receiving chamber is provided with an opening for receiving the penis in the chamber, and means forming a leak-resistant sealed condition around the penis. The urinary collector body further includes a urinary flow chamber located in a second or lower part of the collector body, which urinary flow chamber is separated from the penis receiving chamber by a water permeable membrane. The urinary flow chamber includes a hydrophobic medium, preferably comprising a plurality of hydrophobic beads therein. The hydrophobic beads can comprise granules or small flakes which can have various shapes such as a spherical shape, or a cylindrical, barrel, circular, or outlet opening adjacent the lowermost portion thereof through which the urine can be discharged from the device to other urine receiving and holding means.

The bag shaped urinary collector body is constructed of a flexible material. The location of the plurality of hydrophobic beads adjacent the lower end portion of the urinary collector body acts to maintain the shape of the urinary collector body and positions the hydrophobic beads for receiving and buffering the discharge flow of urine from the penis. This shape maintaining characteristic also enables the penis to be inserted through the opening and into the penis receiving chamber without collapsing or crushing the urinary collector body and pressing the inside wall thereof against the penis. In operation, when urination occurs, the discharged urine is communicated from the penis receiving chamber through the water permeable membrane into the urinary flow chamber, wherein the urine can flow smoothly around the hydrophobic material or beads and through the interstices formed therebetween downwardly through the urinary flow chamber under the influence of gravity without having a tendency of flowing upwardly back into the penis receiving chamber. The urine is discharged from the device through the discharge outlet and into separate urine holding means which can be attached thereto, for instance, a tube communicating with a urinal bag, which separate urine holding means do not form part of the present invention.

It is therefore an object of the present invention to provide a urinary collector for men which attaches directly to the penis and receives and buffers the flow of discharged urine and passes the urine to collecting or holding means.

Another object is to provide a urinary collector for men which buffers the flow of discharged urine without the urine flowing back towards the penis and collecting therearound.

Another object is to provide a urinary collector for men which can maintain the penis in a relatively dry and sanitary condition.

Another object is to provide a urinary collector for men which is quickly and easily attachable and detachable to the body and to undergarments without assistance.

Another object is to provide a urinary collector for men which is comfortable to wear and use.

Another object is to provide a urinary collector for men which can be discretely worn.

Another object is to provide a urinary collector that is not easily compressible or crushable.

Another object is to provide a urinary collector for men which does not increase difficulty or pain during urination for persons suffering from dysuria.

Another object is to provide a urinary collector for dysuriac men which does not increase physical and psychological resistance to urination.

These and other objects and advantages of the present urinary collector for men will become apparent after considering the following specification in conjunction with the accompanying drawings wherein:

DETAILED DESCRIPTION OF THE PREFERRED EMBODIMENTS

The present invention will be explained in detail with reference to the attached drawings.

Figures 1A, 1B:
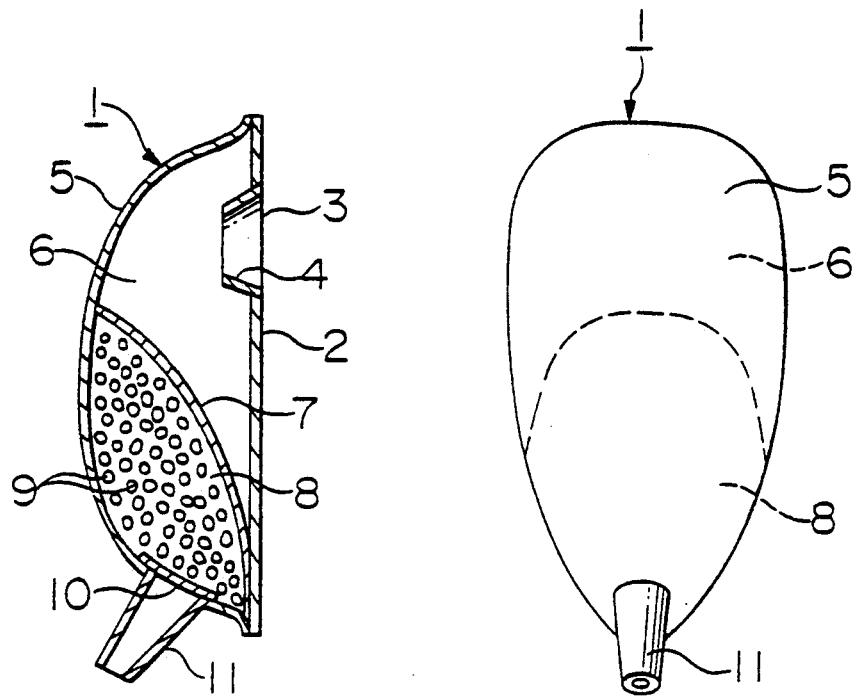
FIGS. 1a, 1b, and 1c are a cross-sectional view, a front elevational view, and a rear elevational view, respectively, of one embodiment of a urinary collector device for men constructed according to the teachings of the present invention.
Figure 1C:
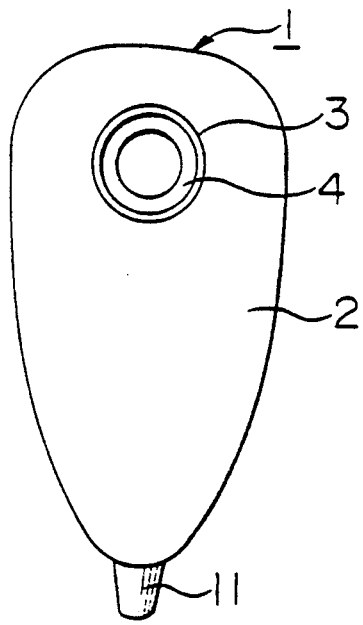

Referring to the drawings more particularly by reference numbers wherein like numerals refer to like parts, FIGS. 1a, 1b, and 1c show one embodiment of a urinary collector device for men wherein the numeral 1 identifies a urinary collector body made of a thin, waterproof and soft material formed into a bag or bag-like shape. The urinary collector body 1 has a first or upper end portion and a second or lower opposite end portion and includes a rear face 2 which is substantially planar in its free state for locating adjacent to a wearer's genitalia. The rear face 2 includes an opening 3 adjacent the upper end portion of the collector body 1, which opening 3 is sized and shaped for receiving a user's penis. An annular tapered sleeve 4 made from a flexible, thin material is located around the opening 3 and extends inwardly and convergingly into the collector body 1. The sleeve 4 cooperatively and comfortably engages the outer surface of a penis inserted into the opening 3 to maintain the penis located therein and forms a leak-resistant sealed condition therearound, as discussed in more detail below.

The urinary collector body 1 has a front face 5 attached to the periphery of the rear face 2 and extending outwardly therefrom forming a convex outer shape which forms an internal cavity in the urinary collector body 1. A penis receiving chamber 6 is provided in the internal cavity adjacent the first or upper end of the collector body 1, and a urinary flow chamber 8 is provided adjacent the second or lower end thereof, which urinary flow chamber 8 is separated from the penis receiving chamber 6 by a water permeable membrane 7 located therebetween.

The urinary flow chamber 8 contains a hydrophobic medium, preferably comprising a plurality of beads 9, which beads 9 are made of a hydrophobic material and are preferably relatively tightly packed into the chamber 8. A urinary discharge outlet opening 11 is located adjacent the lowermost portion of the urinary flow chamber 8, which urinary discharge outlet 11 is covered by a second water permeable membrane 10, which water permeable membrane 10 prevents the hydrophobic beads 9 from passing through the outlet 11. The urinary discharge outlet 11 is an annular shaped member which tapers slightly convergingly towards the free end thereof.

Figure 2A:
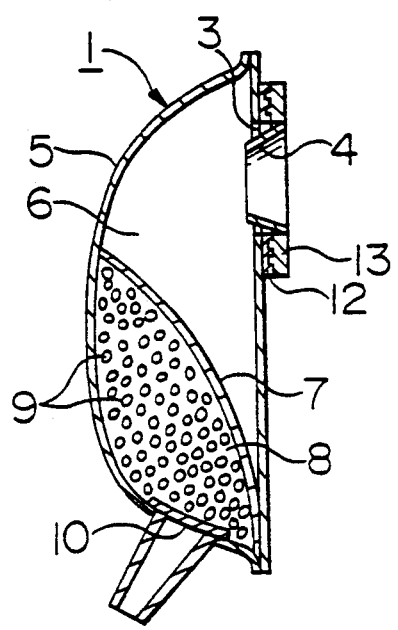
FIGS. 2a and 2b, are a cross-sectional view and a rear elevational view, respectively, of another embodiment of a urinary collector for men.
Figure 2B:
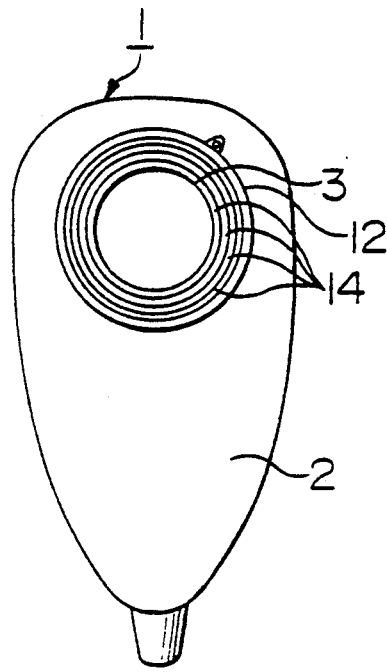
Figure 2C:
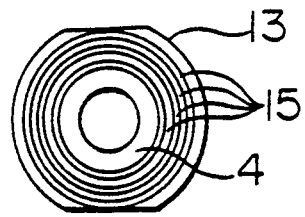
FIG. 2c is a front elevational view of a fitting for use with the urinary collector device of FIGS. 2a and 2b.

FIGS. 2a and 2b show another embodiment of a urinary collector device for men constructed according to the teachings of the present invention, and FIG. 2c shows a ring shaped connector for use with the urinary collector device of FIGS. 2a and 2b. The urinary collector device of FIGS. 2a-c includes many of the same components of the urinary collector device of FIGS. 1a-c and therefore such components share the same numerical designations therefor. The urinary collector device of FIGS. 2a-c differs from that of FIGS. 1a-c in that the urinary collector device of FIGS. 2a-c includes detachable connecting ring means for receiving and attaching to the penis, including a first connecting ring 12 mounted on the rear face 2 around the opening 3 and a separate second connecting ring 13 attachable to the first connecting ring 12 and which connecting ring 13 mounts over a wearer's penis. The connecting ring 12 includes attaching means 14 for joining to the connecting ring 13, comprising concentric annular grooves and prominences cooperatively engageable with attaching means 15 on the second connecting ring 13, which means 15 comprise oppositely facing concentric annular prominences and grooves. Also different, is that the tapered sleeve 4 of the embodiment of FIGS. 2a-c is mounted on the separate second ring 13 instead of directly on the rear face 2, as in the embodiment of FIGS. 1a-c. The advantage of this construction is that it enables the urinary collector body 1 to be removed from a user without removing the sleeve 4 from the user's penis.

Figure 3:
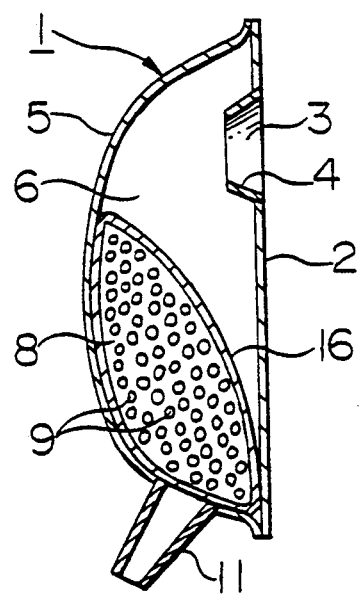
FIG. 3 is a cross-sectional view of still another embodiment of a urinary collector for men constructed acccording to the teachings of the present invention.

FIG. 3 shows still another embodiment of a urinary collector device for men constructed according to the teachings of the present invention. Again, the embodiment of FIG. 3 shares numerous components with the embodiment of FIGS. 1a-c and therefore such components are denoted by the same reference numerals. The embodiment in FIG. 3 differs from that of FIG. 1 in that the collector urinary flow chamber 8 is located in a separate bag 16 located in the urinary body 1, which separate bag 16 is formed by a water permeable membrane and contains the hydrophobic beads 9. The bag 16 is located adjacent the second or lower end of the urinary collector body 1 in position over the urinary discharge outlet 11. The bag 16 can be attached to the body 1 to maintain it in such position, using any suitable means.

The urinary collector body 1 can be fabricated from any suitable material, such as for instance, plastic foam sheet material, flexible plastic sheet material, and the like. The foam sheet material can comprise polyethylene, or ethylene-vinyl acetate copolymer, which are the preferred materials, and can also be fabricated from polypropylene, polyvinyl chloride, polystyrene, polybutadiene, and polyurethane. The foam sheet material should have an expansion ratio from about 5 to 1 to about 50 to 1, and have a thickness from about 0.5 to about 5 mm, and preferably from about 1 to about 2 mm. The alternative flexible plastic sheet material can comprise, for instance, a polyethylene, ethylene-vinyl acetate copolymer, polypropylene, polyvinyl chloride, polyamide/polyethylene composite sheet, or various other composite sheets. The flexible plastic sheet can have a thickness from about 0.03 to about 1 mm.

The water permeable membranes 7 and 10 can comprise any suitable material such as a woven fabric, a nonwoven fabric, a porous plastic sheet, or a plastic net, as desired. The woven and nonwoven fabric alternatives may include, for instance, polyester, polyethylene, polypropylene, rayon and polyurethane materials. The porous plastic sheet can include polyethylene, ethylene-vinyl acetate copolymer and polypropylene materials, and preferably has a pore size from about 0.05 to about 3 mm.

The hydrophobic beads 9 can comprise beads constructed of plastic material such as polyethylene, polystyrene and polypropylene, and the like, and alternatively, ceramics such as glass, the preferred material being of a foam type material constructed of polyethylene, polystyrene or polypropylene. The hydrophobic beads 9 can be provided in a variety of shapes and sizes. For instance, the hydrophobic beads 9 can have a spherical shape having a diameter from about 0.5 to about 5 mm, an elongated columnar shape having a diameter from about 1 to about 5 mm and a length of about 50 mm, a circular shape having an outer diameter from about 5 to about 20 mm, crepe material having a thickness from about 1 to about 6 mm and a length from about 10 to about 30 mm, and a cylindrical shape having an outer diameter from about 3 to about 20 mm with a height from about 5 to about 20 mm. The device can include any number of hydrophobic beads 9, depending on such factors as the quantity of urine for a particular user. For instance, the device can include a quantity of beads 9 corresponding to a volume from about 30 to about 200 cc with a typical volume of about 130 cc. Additionally, hydrophobic beads 9 treated or mixed with a bacteriacide or deodorant can also be used.

The sleeve 4 can be fabricated from any suitable rubber material, polyethylene, ethylene-vinyl acetate copolymer, polyvinyl chloride, polypropylene and polyurethane, with rubber or polyurethane being preferable.

The connecting rings 12 and 13 of the urinary collector embodiment shown in FIGS. 2a-c can be fabricated from polyethylene, ethylene-vinyl acetate copolymer, polyurethane and polyvinyl chloride and the like. The cooperatively engageable portions of the connector rings 12 and 13 can also be of any suitable well known conventional interlocking construction such as found in U.S. Pat. No. 4,419,100, Great Britain Patent No. 1,571,657, and German Patent No. 3,218,092A1.

The required volume of the urinary flow chamber is approximately determined by the required buffer capacity of the urinary flow chamber. The buffer capacity of the urinary flow chamber is approximately determined from the difference between the estimated discharge flow rate possible through the discharge outlet compared to the estimated flow rate of urination. A urinary flow chamber volume can range from about 30 to about 200 cc, with a volume of about 130 cc being typical.

OPERATION

Figure 4:
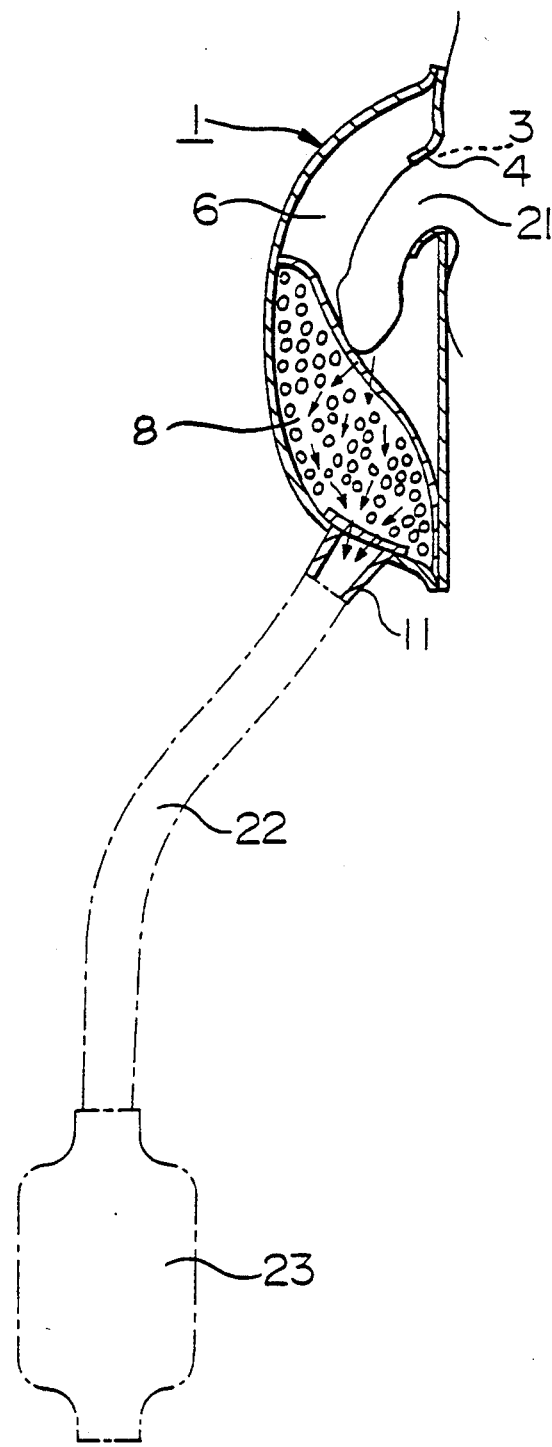
FIG. 4 is a cross-sectional view of the urinary collector for men of FIG. 1, showing the male genitalia, and showing in association with the urinary collector in phantom lines a urinal bag and a connector tube, which urinal bag and connector tube do not form part of the present invention.

The manner of usage and operation of a urinary collector for men such as shown in FIGS. 1a-c and FIG. 3 will be explained referring to FIG. 4. A penis 21 is inserted into the urinary collector body 1 through the opening 3, wherein the sleeve 4 cooperatively receives and is fitted closely to the base of the penis 21 forming a comfortable sealed condition therearound for preventing leakage of urine therearound. When so positioned, a penis 21 is located within the penis receiving chamber 6. Importantly, as the penis is inserted into the penis receiving chamber 6 and engages the sleeve 4, the urinary collector body 1 will maintain its shape without collapsing or crushing as the hydrophobic beads 9 act to maintain the outer shape of the urinary collector body 1. The wearer can then place undergarments (not shown) over the pelvic region with the urinary collector body 1 attached to the genitalia. The outside of the urinary collector body 1 can then be fixed or adhered to the inside of the undergarment by means such as pressure sensitive double coated adhesive tape (not shown). Urine collection means, for instance, a tube 22 connected to a urinal bag 23 can be attached to the discharged outlet 11 of the collector body 1, as shown.

To attach a urinary collector such as shown in FIGS. 2a-c, the second connecting ring 13 is detached from the first connecting ring 12, and the penis inserted through the second connecting ring 13 such that the sleeve 4 is fitted around approximately the base of the penis. The penis can then be inserted into the opening 3 of the collector body 1 and the first connecting ring 12 cooperatively engaged with the second connecting ring 13 to complete attachment of the device, which attachment can be easily accomplished by the wearer himself or by another person.

When urination occurs using any of the above-described embodiments, the urine discharged from the penis can pass readily through the water permeable membrane 7 or 16 into the urinary flow chamber 8 wherein the urine flows down along the surfaces of the hydrophobic beads 9 as shown in the drawing by arrows. Although the urinary collector body 1 is constructed of a soft material, the plurality of hydrophobic beads 9 packed together in the urinary flow chamber 8 acts to maintain the volume of the urinary flow chamber 8. Importantly, the hydrophobic characteristic of the beads 9 facilitates the prompt downward flow of the urine through the urinary flow chamber 8 without absorption of the urine by the beads 9, and importantly, without backward flowing of the urine to the penis receiving chamber 6. In the above described manner, the urinary flow chamber 8 serves as buffer for the urinary flow enabling the smooth discharge of the urine from the outlet 11 and into the urinal bag 23.

A urinary collector for men constructed according to the teachings of the present invention, including an entire urinary collector body fabricated from a waterproof, flexible and soft material and having a urinary flow chamber packed with hydrophobic beads, enables providing a light, small urinary collector device which can be placed compactly and discretely inside a wearer's undergarment without compression or crushing of the device. This reduces discomfort and enables easy attachment by fitting the urinary collector onto the genitalia from the front and by adhering to the wearer's undergarment without requiring typical prior art supporter means such as belts and the like which require more labor for attachment. Detachment of the present device is also similarly made easier. Another important advantage of the present urinary collector is that backflow of urine towards the penis is prevented by the use of a relatively simple structure in the form of the urinary flow chamber containing hydrophobic beads located at an intermediate position in the urinary discharge path. This construction enables urine remaining in the penis receiving chamber to be rapidly absorbed into the urinary flow chamber so as to substantially decrease remaining moisture in the penis receiving chamber. Still further, the structure of the present urinary collector is very simple, inexpensive to produce and enables sanitary usage and disposal. Also importantly, physical and psychological resistance to urination by dysuriac men is substantially lessened by the use of the present urinary collector device.

Thus there has been shown and described several embodiments of a novel urinary collector for men, which constructions fulfill all of the objects and advantages sought therefor. Many changes, modifications, variations, and other uses and applications of the present construction will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A urinary collector for men comprising a urinary collector body made of a waterproof, soft material, formed into a bag shape, said urinary collector body having first and second opposite end portions and defining an internal cavity which forms a penis receiving chamber located adjacent the first opposite end portion and a urinary flow chamber located adjacent the second opposite end portion, a water permeable membrane separating said penis receiving chamber and said urinary flow chamber, said urinary collector body having a penis receiving opening located adjacent the first opposite end portion thereof communicating with said penis receiving chamber enabling insertion of a penis into said penis receiving chamber, means adjacent said penis receiving opening for forming a seal around a penis inserted therein, said urinary collector body further including an outlet opening located adjacent the second opposite end portion thereof, said outlet opening communicating with the urinary flow chamber, hydrophobic material located in said urinary flow chamber, said hydrophobic material having interstices forming passages therethrough enabling urine to pass through said hydrophobic material, and means covering said outlet opening enabling urine to pass through the outlet opening yet preventing said hydrophobic material from passing therethrough.

2. The urinary collector for men according to claim 1 wherein said means for forming a seal around a penis includes an annular sleeve located around said penis receiving opening.

3. The urinary collector for men according to claim 1 wherein said means covering said outlet opening include a water permeable membrane.

4. The urinary collector for men according to claim 2 wherein said annular sleeve is mounted on a ring-shaped member, said ring-shaped member being detachably mounted to said urinary collector body around said penis receiving opening.

5. The urinary collector for men according to claim 1 wherein said hydrophobic material includes a plurality of hydrophobic beads.

6. The urinary collector for men according to claim 5 wherein said hydrophobic beads are constructed of a material selected from the group consisting of polyethylene, polystyrene and polypropylene.

7. The urinary collector for men according to claim 5 wherein said hydrophobic beads are constructed of a ceramic material.

8. A urinary collector for men comprising a urinary collector body made of a waterproof, soft material, formed into a bag shape, the urinary collector body having first and second opposite end portions and defining an internal cavity which forms a penis receiving chamber located adjacent the first opposite end portion thereof and a urinary flow chamber located adjacent the second opposite end portion thereof, a water-permeable membrane separating said penis receiving chamber and said urinary flow chamber, said urinary collector body providing an opening enabling insertion of a penis into said penis receiving chamber, and said urinary collector body providing an outlet opening enabling discharge of urine from said urinary flow chamber therethrough, said urinary flow chamber containing a hydrophobic medium packed therein, said hydrophobic medium having interstices forming passages therethrough, the packed hydrophobic medium in said urinary flow chamber acting to maintain the shape of said urinary collector body, and means adjacent said outlet opening for preventing said hydrophobic medium from passing through said outlet opening yet enabling urine to pass therethrough, a urine flow discharged into said penis receiving chamber passing through said water permeable membrane and into said urinary flow chamber, said urine flow being buffered by passage through said hydrophobic medium and being discharged through said outlet opening.

9. The urinary collector for men according to claim 8 further comprising means for forming a seal around a penis inserted into said penis receiving chamber.

10. The urinary collector for men according to claim 8 wherein said hydrophobic medium is contained in a pouch formed of water permeable material.

11. A urinary collector for men comprising a urinary collector body made of a waterproof, thin, soft material formed into a bag shape, said urinary collector body having first and second opposite end portions and having an interior portion partitioned by a water permeable membrane, aid water permeable membrane dividing said urinary collector body into a penis receiving chamber located adjacent said first opposite end portion and a urinary flow chamber located adjacent said second opposite end portion, said urinary collector body having an opening enabling insertion of a penis therethrough into said penis receiving chamber and having an outlet opening communicating with said urinary flow chamber, said urinary flow chamber containing a plurality of hydrophobic beads packed therein, said hydrophobic beads having passages extending therearound and therebetween, means adjacent said outlet opening preventing said hydrophobic beads from passing through said outlet opening yet enabling urine to pass therethrough, a stream of urine introduced into said penis receiving chamber impinging said water permeable membrane and flowing into said urinary flow chamber, the urine flow being buffered by passage around and between said hydrophobic beads and exiting through said outlet opening.

12. The urinary collector for men according to claim 11 further comprising means adjacent said outlet opening for allowing urine receiving means to be attached thereto.

* * * * *

UNITED STATES PATENT AND TRADEMARK OFFICE
CERTIFICATE OF CORRECTION

PATENT NO. : 5,300,052
DATED : April 5, 1994
INVENTOR(S) : Yoshinori Kubo

It is certified that error appears in the above-indentified patent and that said Letters Patent is hereby corrected as shown below:

Column 8, line 64, "aid" should read --said--.

Signed and Sealed this

Sixteenth Day of August, 1994

Attest:

BRUCE LEHMAN

Attesting Officer

Commissioner of Patents and Trademarks